(12) United States Patent  
Carpenter et al.

(10) Patent No.: US 9,326,758 B2  
(45) Date of Patent: May 3, 2016

(54) FRONT-END LOADER FOR PROSTHETIC OCCLUDERS AND METHODS THEREOF

(75) Inventors: Craig M. Carpenter, Boston, MA (US); Paul A. Garant, Nashua, NH (US); Lee A. Core, Cambridge, MA (US)

(73) Assignee: W.L. Gore & Associates, Inc., Flagstaff, AZ (US)

( * ) Notice: Subject to any disclaimer, the term of this patent is extended or adjusted under 35 U.S.C. 154(b) by 2166 days.

(21) Appl. No.: 10/667,747

(22) Filed: Sep. 22, 2003

(65) Prior Publication Data

US 2004/0133230 A1    Jul. 8, 2004

Related U.S. Application Data

(60) Provisional application No. 60/412,953, filed on Sep. 23, 2002.

(51) Int. Cl.
| | | |
|---|---|---|
| A61M 29/00 | (2006.01) | |
| A61B 17/00 | (2006.01) | |
| A61B 17/12 | (2006.01) | |
| A61B 17/34 | (2006.01) | |
| A61B 17/076 | (2006.01) | |

(52) U.S. Cl.
CPC ....... *A61B 17/0057* (2013.01); *A61B 17/12122* (2013.01); *A61B 17/12172* (2013.01); *A61B 17/076* (2013.01); *A61B 17/3417* (2013.01); *A61B 2017/00575* (2013.01); *A61B 2017/00592* (2013.01); *A61B 2017/00615* (2013.01); *A61B 2017/1205* (2013.01)

(58) Field of Classification Search
CPC ........... A61B 17/0057; A61B 17/3417; A61B 2017/00575; A61B 2017/00592; A61B 2017/1205

USPC ........ 606/194, 200, 191, 192, 213, 215, 216; 623/1.1, 1.11, 2.11, 2.2; 600/184; 604/164.01, 164.02, 164.06, 264, 272

See application file for complete search history.

(56) References Cited

U.S. PATENT DOCUMENTS

| | | | |
|---|---|---|---|
| 4,515,583 A | 5/1985 | Sorich | |
| 4,655,226 A | 4/1987 | Lee | ................. 128/754 |
| 4,921,479 A | 5/1990 | Grayzel | ........................... 604/53 |
| 5,125,902 A | 6/1992 | Berry et al. | .................... 604/164 |
| 5,486,193 A * | 1/1996 | Bourne et al. | ................. 606/194 |
| 5,626,599 A | 5/1997 | Bourne et al. | ................. 606/194 |
| 5,649,950 A | 7/1997 | Bourne et al. | ................. 606/194 |
| 5,746,734 A * | 5/1998 | Dormandy et al. | ............... 606/1 |
| 5,843,028 A | 12/1998 | Weaver et al. | ................... 604/54 |
| 5,846,261 A | 12/1998 | Kotula et al. | ................. 606/213 |
| 5,928,246 A * | 7/1999 | Gordon et al. | ................. 606/108 |
| 5,993,408 A * | 11/1999 | Zaleski | ........................... 604/22 |
| 5,997,562 A | 12/1999 | Zadno-Azizi et al. | |
| 6,053,925 A | 4/2000 | Barnhart | |
| 6,206,871 B1 | 3/2001 | Zanon et al. | ............... 604/891.1 |
| 6,217,566 B1 | 4/2001 | Ju et al. | .......................... 604/526 |
| 6,332,877 B1 | 12/2001 | Michels | ......................... 604/263 |
| 6,592,546 B1 * | 7/2003 | Barbut et al. | .............. 604/96.01 |
| 2002/0099325 A1 | 7/2002 | Sutton et al. | |
| 2002/0169377 A1 * | 11/2002 | Khairkhahan | ....... A61B 5/0084 600/433 |
| 2005/0004648 A1 * | 1/2005 | Boekstegers | ................. 623/1.11 |

* cited by examiner

*Primary Examiner* — Elizabeth Houston  
*Assistant Examiner* — Robert Lynch  
(74) *Attorney, Agent, or Firm* — DLA Piper LLP (US)

(57) ABSTRACT

The invention pertains to a system, and related methods, for the percutaneous transluminal delivery and retrieval of a prosthetic occluder through a front-end loader. The prosthetic occluder may be, for example, an intracardiac occluder for a patent foramen ovale. The system includes, in one embodiment, a front-end loader having a beveled distal end. In another embodiment, the system includes a front-end loader having a chamfered rim at the beveled distal end.

7 Claims, 6 Drawing Sheets

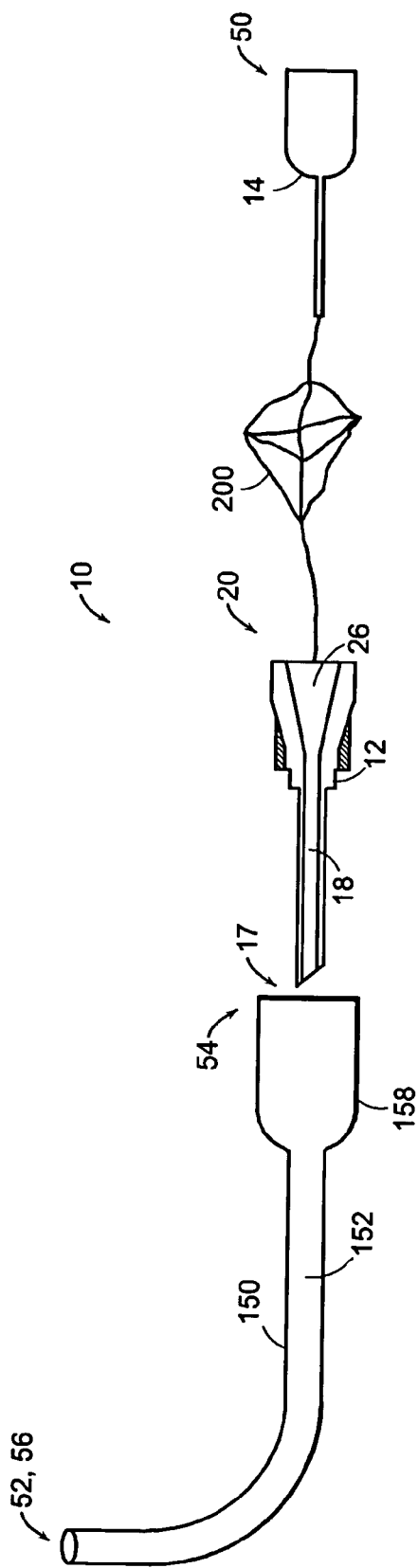
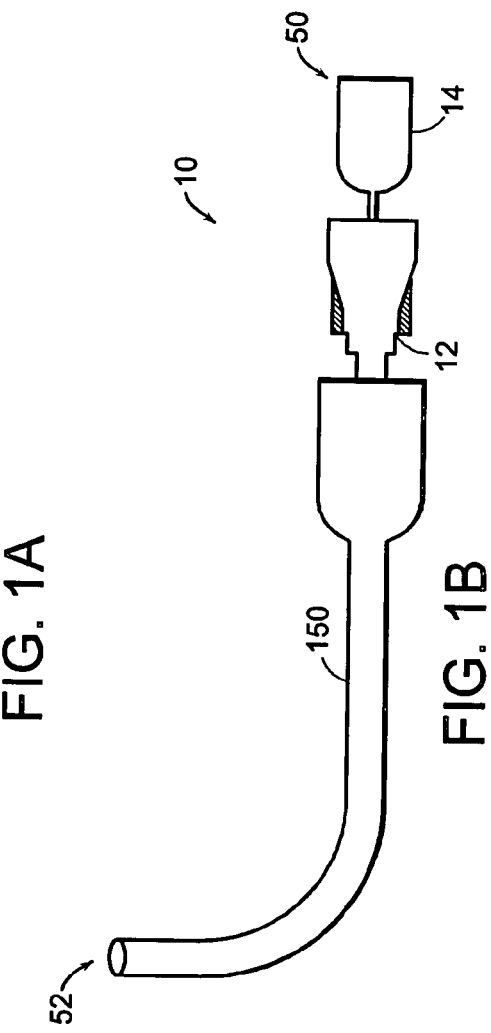
FIG. 1A
FIG. 1B

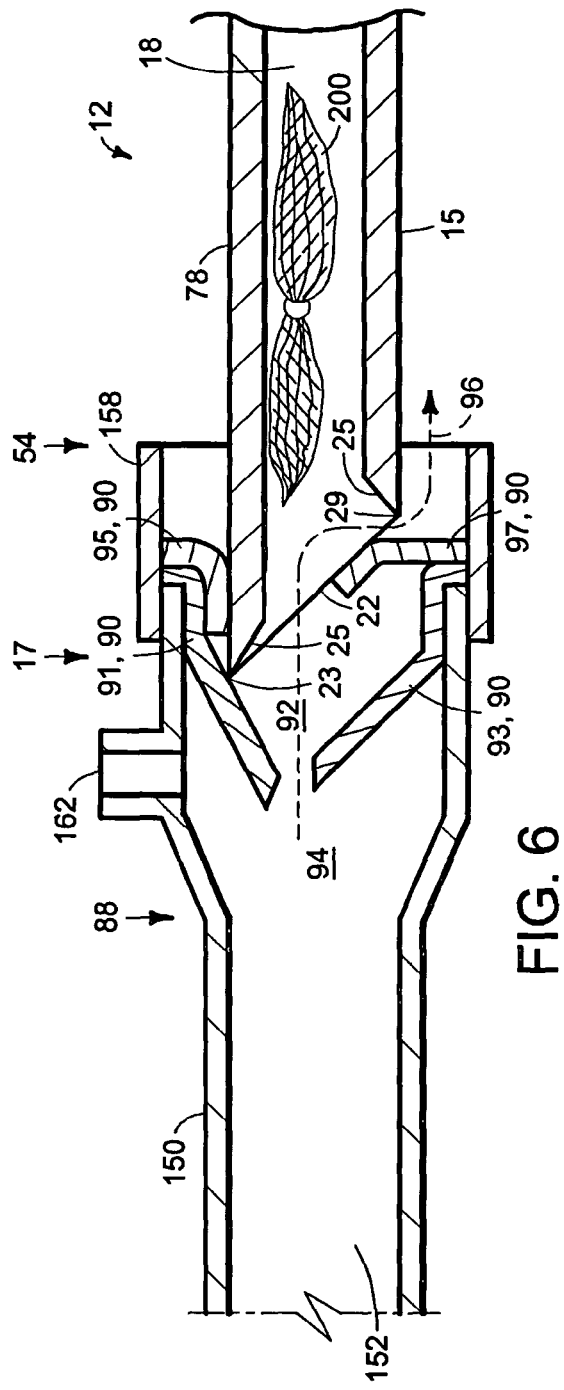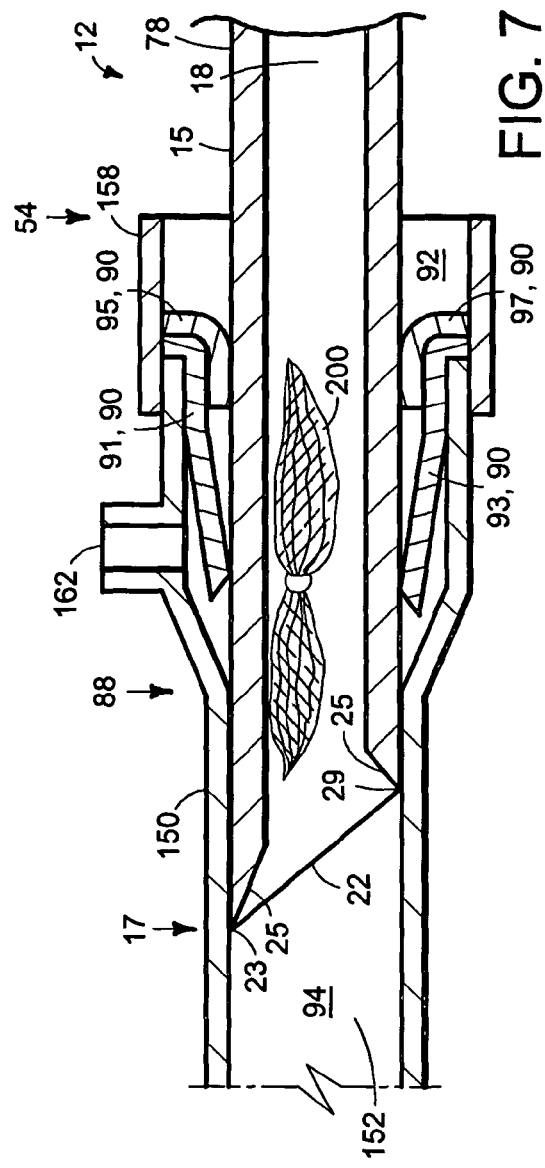

FRONT-END LOADER FOR PROSTHETIC OCCLUDERS AND METHODS THEREOF

CROSS-REFERENCE TO RELATED APPLICATION

This application incorporates by reference, and claims priority to and the benefit of, U.S. provisional application Ser. No. 60/412,953, which was filed on Sep. 23, 2002.

TECHNICAL FIELD

The invention generally relates to a system, and related methods, for the percutaneous transluminal front-end loading delivery and retrieval of devices used to repair cardiac defects. More particularly, the invention relates to an improved front-end loader device.

BACKGROUND INFORMATION

Prosthetic occluders for repairing intracardiac defects, such as interatrial and interventricular septal shunts, patent ductus arteriosus, patent foramen ovale, and occlusion of the left atrial appendage, are well known in the art. Moreover, systems for percutaneous transluminal front-end loading delivery and retrieval of a prosthetic occluder have been described. Representative is "System for the Percutaneous Transluminal Front-End Loading Delivery of a Prosthetic Occluder", U.S. Pat. No. 5,486,193 (Bourne et al.), the entirety of which is expressly incorporated by reference herein, which discloses a complete system including a front-end loading portion, a control assembly, and an introducer.

Significant problems exist, however, with the front-end loaders currently known in the art. A first problem that may arise with current front-end loaders is the introduction of air into the indwelling introducer sheath when the front-end loader is introduced into the hub of the introducer sheath to deliver or retrieve a prosthetic occluder. Air that is introduced into a closed system, such as the introducer sheaths known in the art, may find its way into the patient's cardiovascular system, risking acute pulmonary embolism, myocardial infarction, stroke, and possibly death.

A second problem with current front-end loaders is that they are not well suited, should the need arise, for the retrieval of a prosthetic occluder from the heart or a vessel. Occasionally during a procedure to implant a prosthetic occluder in a patient, the occluder is an improper fit, deploys improperly, or is in some way damaged and must be retrieved from the patient. With current front-end loaders, significant problems often arise in attempting to collapse and withdraw the prosthetic occluder from the lumen of the introducer sheath into the lumen of the front-end loader. For instance, in withdrawing the prosthetic occluder from the lumen of the introducer sheath into the lumen of the front-end loader, the proximal portion of the prosthetic occluder may catch on the distal end of the front-end loader, potentially preventing removal of the occluder. For example, the prosthetic occluder may become snagged on the distal end of the front-end loader, necessitating the removal of the introducer sheath and the front-end loader from the patient in order to remove the occluder. In essence, the prior art lacks a reliable and efficient system for ensuring that the occluder can be withdrawn into the front-end loader so that the introducer sheath will not have to be removed from the patient.

It is, therefore, an object of the present invention to provide a front-end loader that minimizes or eliminates the introduction of air into an indwelling introducer sheath and that facilitates the retrieval of a prosthetic occluder without removal of the indwelling introducer sheath, should the need to do so arise.

SUMMARY OF THE INVENTION

The invention provides a system, and related methods, for the percutaneous transluminal front-end loading delivery and retrieval of a prosthetic occluder to and from, respectively, a patient's heart.

In accordance with the invention, a percutaneous transluminal system for a prosthetic occluder, and related methods, use a front-end loader device comprising a tube to deliver or retrieve prosthetic occluders. The tube of the front-end loader is beveled at its distal end. When the front-end loader is introduced into the hub of an indwelling introducer sheath, the beveled end serves to minimize or eliminate the introduction of air into the introducer sheath. Additionally, the beveled distal end of the tube of the front-end loader is chamfered, either partly or entirely, around its rim. The chamfered rim facilitates the removal of a prosthetic occluder from the patient's body, should the need to do so arise.

In one aspect, the invention includes a percutaneous transluminal system for a prosthetic occluder, including a front-end loader. The front-end loader has a proximal portion that includes an expanded lumen, and a distal portion that includes a tube. The tube has a proximal end, a distal end, and a lumen that extends from the proximal end to the distal end. The distal end of the tube is beveled to form a beveled end. The beveled end receives the prosthetic occluder.

In various embodiments of this aspect of the invention, the beveled end may be chamfered. The chamfering may occur partially or, alternatively, entirely around the perimeter of the distal end of the tube. In another embodiment, the expanded lumen of the proximal portion of the front-end loader may be tapered. Moreover, the expanded tapered lumen may be conically shaped. In an additional embodiment, the beveled end receives the prosthetic occluder to withdraw it from a patient's body or the beveled end receives the prosthetic occluder to deliver it into the patient's body. For example, the beveled end receives the prosthetic occluder through the distal end of the tube. The prosthetic occluder may be an intracardiac occluder used to treat, for example, an atrial septal defect, a ventricular septal defect, patent ductus arteriosus, patent foramen ovale, or occlusion of the left atrial appendage.

In another aspect, the invention includes a percutaneous transluminal system for a prosthetic occluder, including a front-end loader. The front-end loader has a proximal portion that includes an expanded lumen, and a distal portion that includes a tube. The tube has a proximal end, a distal end, a lumen that extends from the proximal end to the distal end, and a chamfered rim. The chamfered rim is positioned at the distal end of the tube, which receives the prosthetic occluder.

In various embodiments of this aspect of the invention, the distal end of the tube is beveled. The chamfered rim may be chamfered partially or, alternatively, entirely around the perimeter of the distal end of the tube. In another embodiment, the expanded lumen of the proximal portion of the front-end loader may be tapered. Moreover, the expanded tapered lumen may be conically shaped. In an additional embodiment, the distal end of the tube receives the prosthetic occluder to withdraw it from a patient's body or the distal end receives the prosthetic occluder to deliver it into the patient's body. For example, the distal end of the tube receives the prosthetic occluder through the distal end. The prosthetic occluder may be an intracardiac occluder used to treat, for example, an atrial septal defect, a ventricular septal defect, patent ductus arteriosus, patent foramen ovale, or occlusion of the left atrial appendage.

In another aspect, the invention provides a method for delivering a collapsible prosthetic occluder to a patient. The method includes the step of providing a front-end loader according to the invention described above. The method further includes the steps of receiving the prosthetic occluder in the lumen of the tube and delivering the prosthetic occluder to the patient. In an embodiment of this aspect of the invention, the method may further include the step of introducing the beveled end of the front-end loader into the lumen of a portion of an introducer sheath for the prosthetic occluder and crossing a gland.

In yet another aspect, the invention provides a method for retrieving a collapsible prosthetic occluder from a patient. The method includes the step of providing a front-end loader according to the invention described above. The method further includes the steps of receiving the prosthetic occluder in the lumen of the tube and retrieving the prosthetic occluder from the patient.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 1A is a fragmented plan view of one embodiment of the percutaneous transluminal front-end loading delivery and retrieval system according to the invention.

FIG. 1B is an assembled plan view of the percutaneous transluminal front-end loading delivery and retrieval system illustrated in FIG. 1A.

FIG. 6 is a plan view of the distal end of the front-end loader illustrated in FIG. 5 positioned within the lumen of the proximal end of the introducer sheath illustrated in FIG. 5.

FIG. 7 is a plan view of the distal end of the front-end loader illustrated in FIG. 6 further positioned within the lumen of the proximal end of the introducer sheath illustrated in FIG. 6.

DETAILED DESCRIPTION OF THE INVENTION

Figure 2:
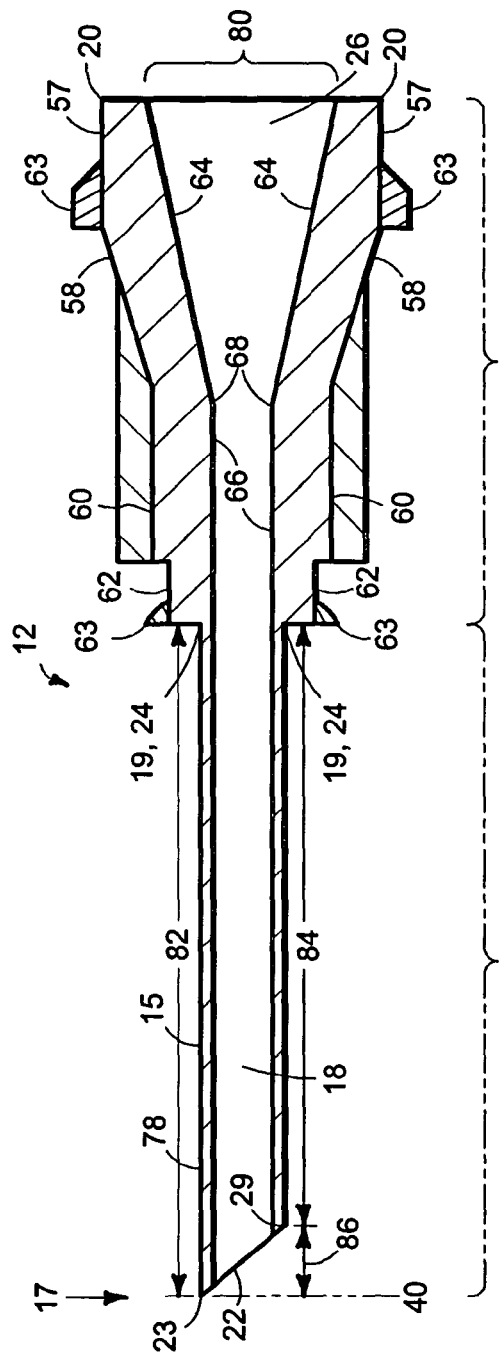
FIG. 2 is a cross-sectional view of one embodiment of the front-end loader illustrated in FIG. 1A.

The invention pertains to a system, and related methods, for the percutaneous transluminal front-end loading delivery and retrieval of a prosthetic occluder. Prosthetic occluders may be used to repair congenital or acquired defects (shunts) in the heart or the major blood vessels thereof, including interatrial and interventricular septal shunts, such as a patent foramen ovale, patent ductus arteriosus, and occlusion of the left atrial appendage.

Referring to FIG. 1A, the percutaneous transluminal front-end loading delivery and retrieval system 10, according to the invention described herein, includes a control assembly 14, a front-end loader 12, and an introducer sheath 150. The control assembly 14, the front-end loader 12, and the introducer sheath 150 are, as shown, separate components.

Referring now to FIG. 1B, when joined together in an assembled state, the control assembly 14 is located at the proximal end 50 of the percutaneous transluminal front-end loading delivery and retrieval system 10, i.e., at the end of the delivery and retrieval system 10 that is closest to an operator (e.g., a physician). The introducer sheath 150 is located at the distal end 52 of the delivery and retrieval system 10 and the front-end loader 12 is positioned between the control assembly 14 and the introducer sheath 150.

Referring again to FIG. 1A, in one embodiment according to the invention, the front-end loader 12 has a proximal end 20, a distal end 17, and a first lumen 26 proximal to and joined to a second lumen 18. Together, the first lumen 26 and the second lumen 18 extend from the proximal end 20 of the front-end loader 12 to the distal end 17 of the front-end loader 12. The first lumen 26 is conically shaped and wider than the second lumen 18. Alternatively, in another embodiment, the front-end loader 12 includes one lumen. For example, the front-end loader 12 includes but one lumen that narrows from the proximal end 20 of the front-end loader 12 to the distal end 17 of the front-end loader 12. For its part, the introducer sheath 150 has a proximal end 54, a distal end 56, and a lumen 152 extending from the proximal end 54 to the distal end 56. The introducer sheath 150 may include, at its proximal end 54, a hub 158.

In general, the introducer sheath 150 is inserted, at its distal end 56, into a patient's body and advanced until the distal end 56 reaches a defect site in the patient's body, such as the heart. In one embodiment, an occluder 200, for example, a septal occluder as described in U.S. Pat. Nos. 5,709,707; 5,425,744; and 5,451,235, is loaded into the first lumen 26 of the front-end loader 12 at its proximal end 20. Optionally, prior to loading the occluder 200 into the first lumen 26, the operator collapses the occluder 200, or a portion thereof. In one embodiment, the operator collapses the occluder 200, or a portion thereof, by drawing on, for example, sutures attached to the occluder 200. Once placed in the first lumen 26 of the front-end loader 12, the operator then advances the occluder 200 from the conically shaped first lumen 26 to the narrower second lumen 18, thereby further collapsing the occluder 200 into a narrow configuration within the second lumen 18 of the front-end loader 12 at its distal end 17. Alternatively, in another embodiment, the occluder 200 may be loaded directly into the second lumen 18 of the front-end loader 12 at its distal end 17. Once in the narrow collapsed configuration, the occluder 200 may be flushed by infusing an appropriate solution, such as, for example, sterile saline and/or heparin, through the first lumen 26 and the second lumen 28. Such flushing of the occluder 200 eliminates any air that is trapped within the occluder 200 itself. The occluder 200 is then in a suitable configuration and state for loading into the lumen 152 of the indwelling introducer sheath 150 at its proximal end 54. The distal end 17 of the front-end loader 12, enclosing the occluder 200, is inserted into the lumen 152 of the hub 158 at the proximal end 54 of the previously placed indwelling introducer sheath 150. The control assembly 14 is used to advance the occluder 200 from the second lumen 18 of the front-end loader 12 into and throughout the lumen 152 of the indwelling introducer sheath 150. At the distal end 56 of the indwelling introducer sheath 150, which has already been positioned near the defect site in the patient's body, such as the heart, the occluder 200, through actuation of the control assembly 14, is released and deployed from the lumen 152 of the indwelling introducer sheath 150 in a fully expanded open configuration.

Referring now to FIG. 2, the front-end loader 12 includes an expanded proximal portion 21 and an elongated distal portion 27. The expanded proximal portion 21 has a proximal end 20, a distal end 19, and a first lumen 26 extending from the proximal end 20 to the distal end 19. In one embodiment according to the invention, the expanded proximal portion 21 includes a first outer surface 57, a second outer surface 58, a third outer surface 60, and a fourth outer surface 62. The first outer surface 57 and the fourth outer surface 62 are each substantially similar to the outer surface of a short cylinder. The second outer surface 58 is substantially similar to the outer surface of a lower portion of a cone and the third outer surface 60 is substantially similar to the outer surface of a longer cylinder. The first outer surface 57 and the fourth outer surface 62 can include any number of threadable engagements 63 extending therefrom. The threadable engagements 63 may be used to engage corresponding receivable threads on the hub 158. In alternative embodiments, the expanded proximal portion 21 can include any number of outer surfaces that are substantially similar to any geometrical shape, each with or without any number of threadable engagements 63 extending therefrom.

As illustrated in FIG. 2, in one embodiment of the expanded proximal portion 21, the expanded proximal portion 21 includes a first inner surface 64 and a second inner surface 66. The first inner surface 64 extends from the proximal end 20 of the expanded proximal portion 21 to an end point 68, which is located proximal to the distal end 19 of the expanded proximal portion 21. The second inner surface 66 extends from the end point 68 to the distal end 19 of the expanded proximal portion 21. In the embodiment shown, the first lumen 26 narrows from the proximal end 20 of the expanded proximal portion 21 to the end point 68 by tapering. In one embodiment, the first inner surface 64 may be shaped substantially similar to the inner surface of a hollow cone. Alternatively, the first inner surface 64 may be shaped substantially similar to the inner surface of a hollow triangular prism.

The end point 68 may be positioned at any point along the long axis of the expanded proximal portion 21. In another embodiment of the expanded proximal portion 21, the end point 68 is positioned substantially equal with the distal end 19 of the expanded proximal portion 21. The expanded proximal portion 21 includes only the first inner surface 64, and not also the second inner surface 66, and the first lumen 26 narrows from the proximal end 20 of the expanded proximal portion 21 all the way to the distal end 19 of the expanded proximal portion 21 by tapering. Again, the first inner surface 64 may be shaped substantially similar to the inner surface of a hollow cone. Alternatively, the first inner surface 64 may be shaped substantially similar to the inner surface of a hollow triangular prism.

In yet another embodiment, the expanded proximal portion 21 may include multiple inner surfaces and the first lumen 26 may narrow from the proximal end 20 to the end point 68, or, alternatively, the distal end 19, in a stepwise fashion. The degree by which the first lumen 26 narrows may be, but need not be, equal on each step.

Referring still to FIG. 2, in one embodiment of the elongated distal portion 27, the elongated distal portion 27 includes a tube 15 with a proximal end 24, a distal end 17, and a second lumen 18 extending from the proximal end 24 to the distal end 17. In the embodiment shown, the proximal end 24 of the tube 15 is positioned substantially equal with the distal end 19 of the expanded proximal portion 21. In such an embodiment, the tube 15 and the expanded proximal portion 21 form one integral component. In another embodiment, the proximal end 24 of the tube 15 is positioned proximal to the distal end 19 of the expanded proximal portion 21, but distal to the end point 68. In such an embodiment, the tube 15 is a separate component from the expanded proximal portion 21. The proximal end 24 of the tube 15 is fitted within the lumen 26 of the expanded proximal portion 21 at its distal end 19 and is fixed to the second inner surface 66 of the expanded proximal portion 21 by, for example, an adhesive or molten plastic.

In one embodiment according to the invention, a cross-section of the outer surface 78 of the tube 15, taken at a point between the proximal end 24 and a base 29 of the tube 15, is circular. Alternatively, a cross-section of the outer surface 78 of the tube 15, taken at a point in the appropriate aforementioned range, may be shaped like any other geometrical shape, including, but not limited to, a triangle, a square, a rectangle, a parallelogram, a semi-circle, an ellipse, a wedge, or a diamond.

The second lumen 18 of the tube 15 is narrower than the broadest portion 80 of the first lumen 26 of the expanded proximal portion 21. The second lumen 18 of the tube 15 is sized to compress the occluder 200 (see FIG. 1A) to a predetermined cross-sectional area, such that the occluder 200 is compatible for insertion into the lumen 152 of the introducer sheath 150 at its proximal end 54 (see FIG. 1A).

In one embodiment, a cross-section of the second lumen 18 of the tube 15, taken at a point between the proximal end 24 and the base 29 of the tube 15, and/or of the first lumen 26 of the expanded proximal portion 21, taken at a point between the end point 68 and the distal end 19 of the expanded proximal portion 21, is circular. In alternative embodiments, a cross-section of the second lumen 18 of the tube 15 and/or of the first lumen 26 of the expanded proximal portion 21, each respectively taken at a point in the appropriate aforementioned range, may be shaped like any other geometrical shape, including, but not limited to, a triangle, a square, a rectangle, a parallelogram, a semi-circle, an ellipse, a wedge, or a diamond.

With continued reference to FIG. 2, the distal end 17 of the tube 15 of the elongated distal portion 27 of the front-end loader 12 is trimmed transversely at an angle in the range greater than 0 degrees to about 75 degrees, preferably 45 degrees, from a line 40 drawn perpendicular to the long axis of the tube 15 of the elongated distal portion 27 to form a beveled end 22. The beveled end 22 of the tube 15 of the elongated distal portion 27 has a tip 23 and the base 29, which is proximal to the tip 23. The distance 82 between the distal end 19 of the expanded proximal portion 21 and the tip 23 of the beveled end 22 of the tube 15 is in the range of 1 to 4 inches, preferably about 2½ inches. The distance 84 between the distal end 19 of the expanded proximal portion 21 and the base 29 of the beveled end 22 of the tube 15 is in the range of $9/10$ to $3^{63}/64$ inches, preferably about $2^{9}/20$ inches. The distance 86 between the base 29 and the tip 23 of the beveled end 22 of the tube 15 is in the range of $1/64$ to $1/10$ of an inch, preferably about $1/20$ of an inch.

Figure 3:
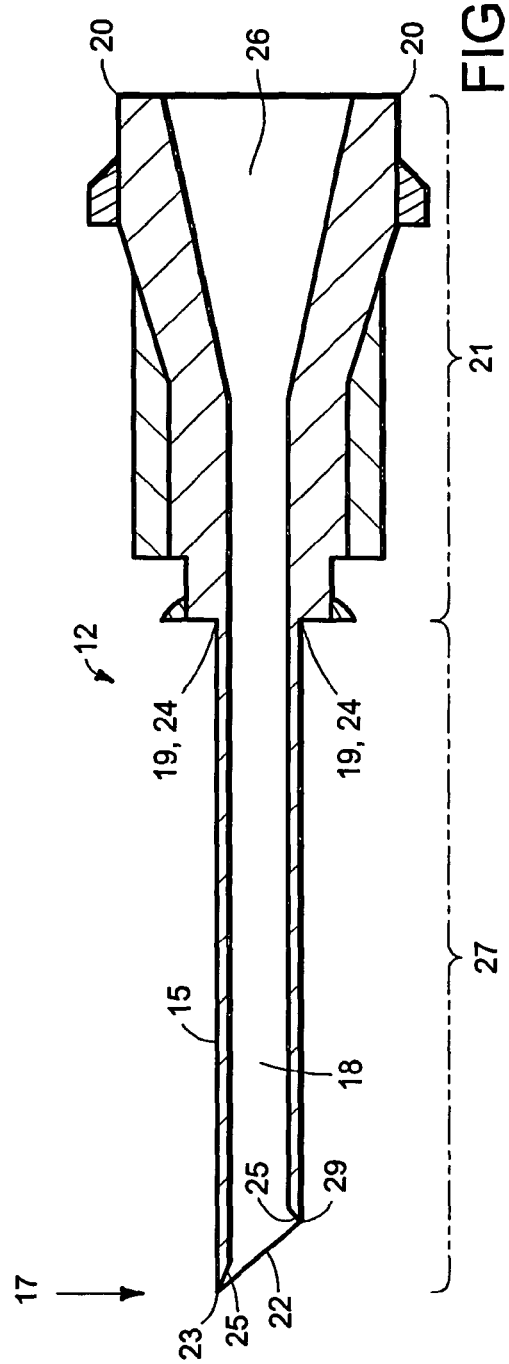
FIG. 3 is a cross-sectional view of another embodiment of the front-end loader illustrated in FIG. 1A.

Referring now to FIG. 3, in one embodiment according to the invention, the distal end 17 of the tube 15 of the elongated distal portion 27 is trimmed transversely to form the beveled end 22 and its rim 25 is also chamfered to form a chamfered rim 25. In an alternative embodiment (not shown), the rim 25 of the distal end 17 of the tube 15 is chamfered, but the distal end 17 of the tube 15 is not also trimmed transversely at an angle from the line 40 (see FIG. 2). Rather, the distal end 17 of the tube 15 is a straight edge cut perpendicular to the long axis of the front-end loader 12 (i.e., the distal end 17 of the tube 15 is trimmed transversely so that the distal end 17 is flush with the line 40). Accordingly, in this latter alternative embodiment, the front-end loader 12 includes the chamfered rim 25, but it does not also include the beveled end 22.

Figure 4:
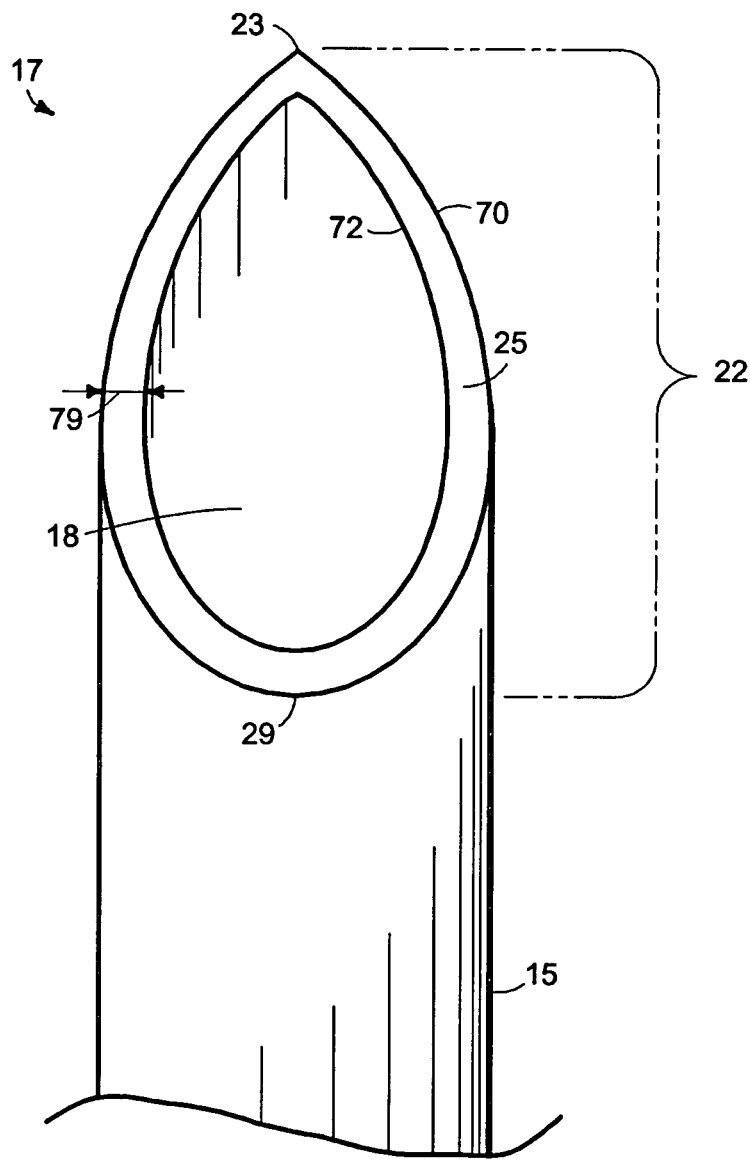
FIG. 4 is a perspective end view of one embodiment of the distal end of the front-end loader illustrated in FIG. 3.

Referring now to FIG. 4, in one embodiment, the chamfered rim 25 is chamfered around the entire perimeter of the distal end 17 of the tube 15. The chamfered rim 25 includes an outer rim 70 and an inner rim 72. The width 79 of the chamfered rim 25, measured from the inner rim 72 to the outer rim 70, is in the range of $5/1000$ to $30/1000$ of an inch, preferably about $15/1000$ of an inch. The size of the tube 15 of the elongated distal portion 27 is in the range of 4 French to 15 French.

In one embodiment according to the invention, the width 79 of the chamfered rim 25 is substantially uniform around the entire perimeter of the distal end 17 of the tube 15. In another embodiment, the width 79 of the chamfered rim 25 is not uniform, but varies, around the perimeter of the distal end 17 of the tube 15. In yet another embodiment, the distal end 17 of the tube 15 is chamfered only partly around its perimeter, either in one continuous section or intermittently.

Referring again to FIG. 2, the tube 15 of the elongated distal portion 27 may be made from suitable plastic materials (e.g., polytetrafluoroethylene (PTFE), other polymers and copolymers, polyurethane, polycarbonate, polyethylene, nylon, and polyether block amides, such as the Pebax® brand sold by Elf Atochem) and/or from suitable metals (e.g., stainless steel). In one embodiment, the tube 15 of the elongated distal portion 27 may primarily be made from suitable plastic materials, with the distal end 17 of the tube 15 of the elongated distal portion 27 reinforced by metal.

In another aspect, the invention provides a method for introducing and retrieving an implant to and from, respectively, an anatomical site in a patient. The implant, in one embodiment, is the intracardiac occluder 200. The invention, for example, is a method for implanting and retrieving the intracardiac occluder 200 destined to occlude a septal defect, such as, for example, a patent foramen ovale. Briefly, the procedure involves cannulating the right femoral vein with an 8 French introducer sheath and then manipulating a 7 French end hole angiocatheter to the right heart. An angiocardiogram may be performed to determine the anatomy of the septal defect (e.g. the patent foramen ovale). An exchange guidewire is then passed through the angiocatheter and the septum is crossed with the guidewire and, optionally, the angiocatheter. With the guidewire placed across the septal defect (e.g., the patent foramen ovale), the angiocatheter is replaced with the introducer sheath 150. The introducer sheath 150 is advanced over the guidewire through the right heart so that the distal end 56 of the introducer sheath 150 lies in the left atrium. To facilitate steering and manipulation of the assembly, the flexible distal end 56 of the introducer sheath 150 may be pre-bent to conform to the anatomy within the heart. The exchange guidewire, and a dilator if used to predilate the vascular route, are removed and the introducer sheath 150 is flushed to eliminate air and any clots.

Figure 5:
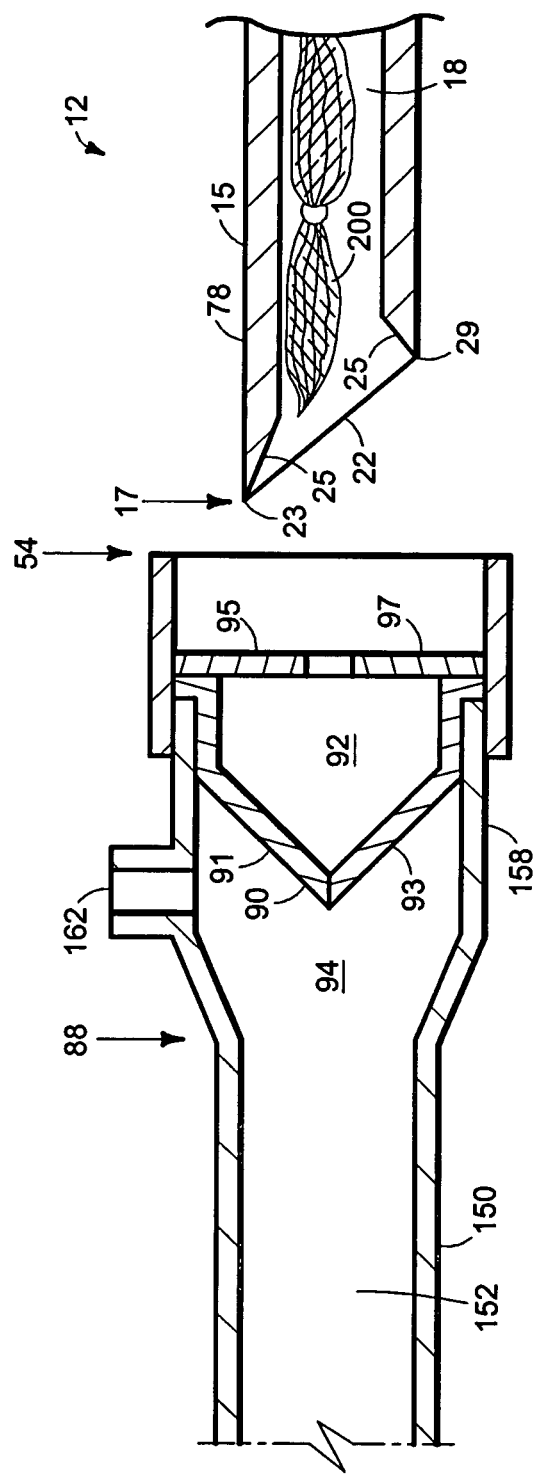
FIG. 5 is a plan view of one embodiment of the distal end of the front-end loader according to the invention positioned near one embodiment of the proximal end of the introducer sheath according to the invention.

Referring now to FIG. 5, in one embodiment according to the method of the invention, the hub 158 of the indwelling introducer sheath 150 includes a proximal end 54, a distal end 88, and a gland 90. In the exemplary embodiment shown, the gland 90 is a resilient elastomer and includes distal portions 91, 93 and proximal portions 95, 97. Before introduction of the front-end loader 12, the distal portions 91, 93 of the gland 90 are pressure sealed together by blood 94, which is located distal to the distal portions 91, 93 of the gland 90. Air 92 is located proximal to the distal portions 91, 93 of the gland 90. The initially sealed distal portions 91, 93 of the gland 90 prevent the air 92 from penetrating distally beyond the distal portions 91, 93 of the gland 90 and further into the indwelling introducer sheath 150.

Referring now to FIG. 6, in one embodiment according to the method of the invention, the distal end 17 of the tube 15 of the front-end loader 12 is inserted into the hub 158. As the distal end 17 of the tube 15 is inserted into the hub 158, the beveled end 22 of the tube 15 first crosses through the proximal portions 95, 97 of the gland 90. The tip 23 of the beveled end 22 of the tube 15 then separates the distal portion 91 of the gland 90 from the distal portion 93 of the gland 90 and the beveled end 22 of the tube 15 crosses through the distal portions 91, 93 of the gland 90. As the beveled end 22 of the tube 15 crosses through the distal portions 91, 93 of the gland 90, the beveled end 22 permits the blood 94 to flow proximally through the gland 90 and, eventually, out of the proximal end 54 of the introducer sheath 150, as indicated by arrow 96. The proximal flow of the blood 94 displaces the air 92 proximally and, eventually, displaces the air 92 from the proximal end 54 of the introducer sheath 150, as indicated by arrow 96. As such, the air 92 is prevented from advancing distally beyond the distal portions 91, 93 of the gland 90 and further into the introducer sheath 150. Thus, the introduction of the air 92 into the vasculature through the introducer sheath 150 can be reduced or eliminated. In the absence of the beveled end 22 of the tube 15 of the front-end loader 12 (i.e., where the distal end 17 of the tube 15 is a straight edge cut perpendicular to the long axis of the front-end loader 12, as in the prior art), air 92 might otherwise percolate into the artery into which the introducer sheath 150 has been placed and thereby create a risk of air embolism.

Referring now to FIG. 7, as the front-end loader 12 is advanced further into the introducer sheath 150, the distal portions 91, 93 and proximal portions 95, 97 of the gland 90 seal around the outer surface 78 of the tube 15 of the front-end loader 12, thereby preventing any further introduction of air 92 into the vasculature via the indwelling introducer sheath 150 and any further proximal flow of blood 94 out of the proximal end 54 of the indwelling introducer sheath 150. Once the distal end 17 of the tube 15 of the front-end loader 12 is positioned beyond the distal end 88 of the hub 158, the occluder 200, previously collapsed, as described above, into a narrow configuration within the second lumen 18 of the tube 15, is ready to be introduced, through actuation of the control assembly 14 (see FIG. 1A), from the second lumen 18 of the tube 15 into the lumen 152 of the introducer sheath 150. The control assembly 14, located proximal to the front-end loader 12 and outside of the patient, is advanced by the operator distally into and through the first lumen 26 and second lumen 18 of the front-end loader 12 to extend the narrowly collapsed occluder 200 from the second lumen 18 of the tube 15 into the lumen 152 of the introducer sheath 150. Optionally, the introducer sheath 150 may, at this point, be flushed by infusing an appropriate solution through a side leg 162 of the introducer sheath 150. The occluder 200 may then be advanced, by the control assembly 14, throughout the lumen 152 of the indwelling introducer sheath 150.

Figure 8A:
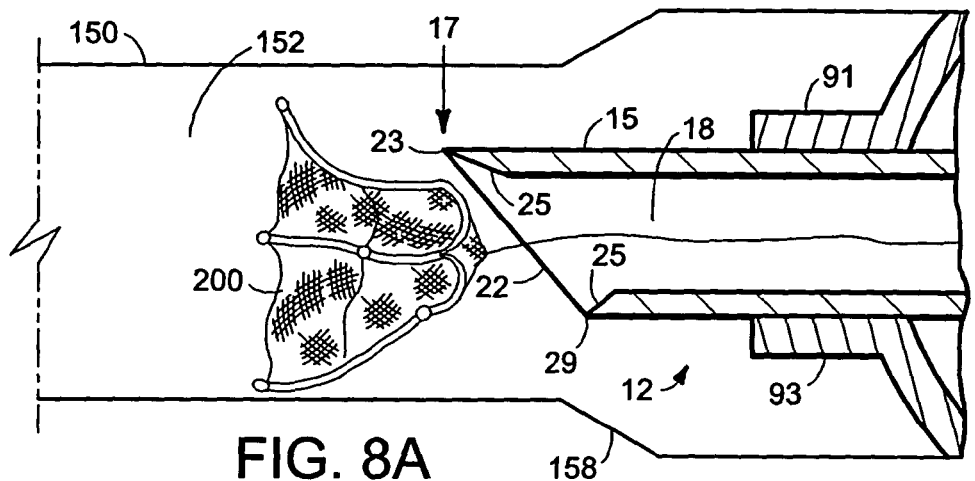
FIGS. 8A-8C illustrate the stages, during one embodiment of a retrieval of a prosthetic occluder from a patient, for collapsing the prosthetic occluder in the front-end loader according to the invention.

In certain circumstances, such as when fluoroscopy or other imaging methods reveal that the occluder 200 is damaged or too small to seal the defect under repair, retrieval of the occluder 200 is required. In order to remove the occluder 200 from the patient with minimal blood loss, the occluder 200 must be withdrawn from the lumen 152 of the introducer sheath 150 into the front-end loader 12. Referring now to FIG. 8A, in one embodiment according to the method of the invention, the occluder 200 may be withdrawn from the lumen 152 of the introducer sheath 150 into the second lumen 18 of the tube 15 of the front-end loader 12.

Figure 8B:
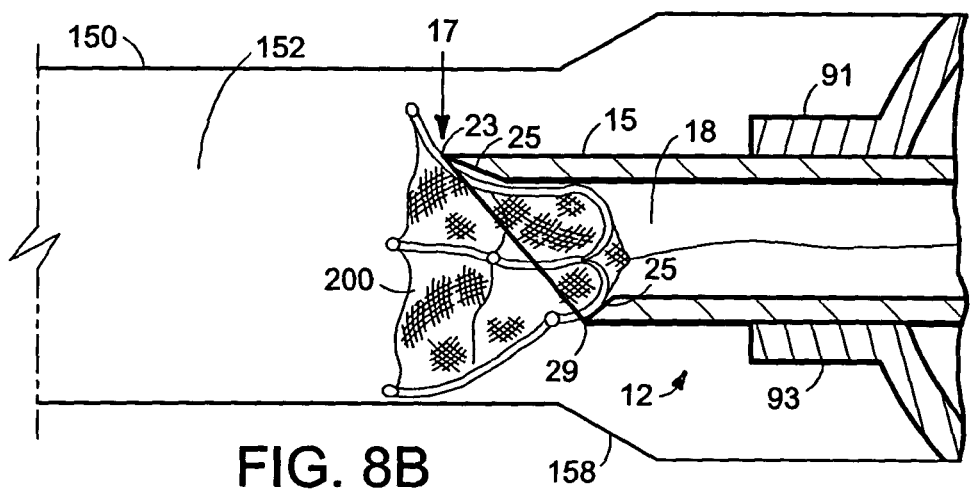

Referring to FIG. 8B, by proximally withdrawing the control assembly 14, the occluder 200 is withdrawn proximally into the second lumen 18 of the tube 15 at the distal end 17 of the front-end loader 12. The occluder 200 enters the second lumen 18 of the tube 15 by sliding through the opening defined by the chamfered rim 25 at the distal end 17 of the tube 15. Because the occluder 200 slides over the smooth slope of the chamfered rim 25 as it enters the second lumen 18 of the tube 15, the chamfered rim 25 eases retrieval of the occluder 200. With the chamfered rim 25 at the distal end 17 of the tube 15, the occluder 200 is much less likely to catch or snag on the distal end 17 of the tube 15 during retrieval than it is in the absence of the chamfered rim 25. The inability to withdraw the occluder 200 into the second lumen 18 of the tube 15 during an attempted retrieval is, therefore, less likely to result.

Figure 8C:
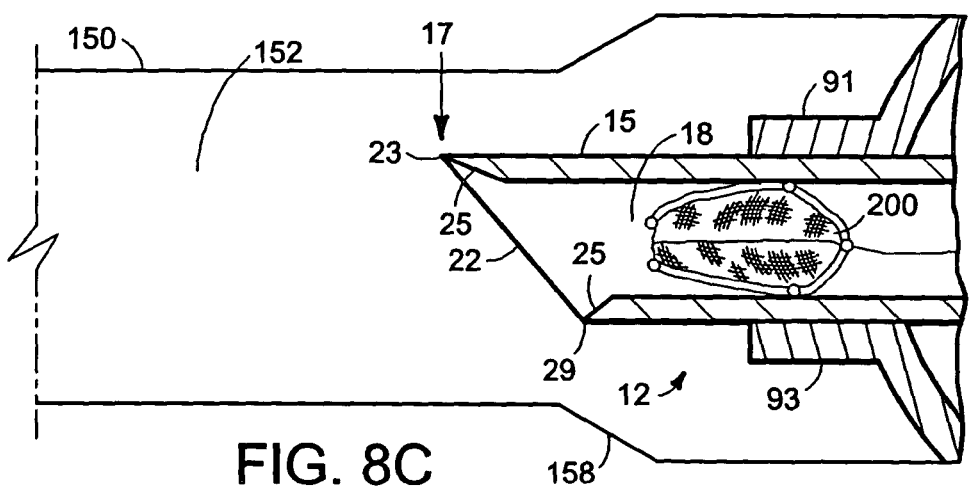

Referring now to FIG. 8C, once the occluder 200 is proximally withdrawn past the base 29 of the beveled end 22 of the tube 15, the front-end loader 12 may be completely withdrawn, through the gland 90 of the hub 158, from the introducer sheath 150.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A percutaneous transluminal system for an intracardiac device having a front-end loader and an introducer sheath having a hub disposed therein, wherein:
   said front-end loader comprises:
   a proximal portion comprising a proximal end, a distal end, and an expanded lumen positioned therebetween, said expanded lumen having a conical shape and a constantly tapering diameter from said proximal end of said proximal portion to said distal end of said proximal portion; and
   a distal portion, comprising a tube comprising a proximal end, a distal end, a lumen extending therethrough, said lumen of said distal portion being co-extensive with said expanded lumen of said proximal portion;
   wherein said distal end of said distal portion comprises means for reducing air introduction into a patients' cardiovascular system when said percutaneous transluminal system is in use during delivery of said intracardiac device from said lumen of said distal portion,
   wherein the means for reducing air introduction includes a beveled edge at said distal end of said distal portion, said beveled edge including a tip and a base, said base disposed proximally of said tip and said edge defining up to a 75 degree angle,
   wherein said beveled edge is chamfered around its entire perimeter, said chamfer defining an opening through said distal end of said distal portion, the chamfer comprising an outer rim and an inner rim and having a width therebetween, said inner rim positioned proximal to said outer rim, and wherein said width between said outer rim and said inner rim is substantially the same or varies about the entire perimeter; and,
   said hub within the introducer sheath comprises:
   a lumen and a gland disposed therein, wherein the gland is an elastomeric polymer defined by opposing proximal portions extending substantially horizontally from the inner wall of the lumen and distal portions extending from the inner wall of the lumen, wherein one such distal portion defines a slope corresponding to the beveled edge; and wherein further the beveled edge of the distal portion of the loader is sized to be insertable through said opposing proximal portions and said opposing distal portions of the gland, so both the proximal and distal portions of the gland remain engaged and sealed to the distal portion of the loader after the beveled edge passes therethrough;
   and wherein further the introducer sheath and the hub have corresponding threaded engagements to secure one to the other.

2. The front-end loader of claim 1, wherein said means for reducing air introduction receives said intracardiac device to withdraw said intracardiac device from the patient's body.

3. The front-end loader of claim 1, wherein said intracardiac device comprises an intracardiac occluder.

4. The front-end loader of claim 3, wherein said intracardiac occluder comprises an occluder for treating an atrial septal defect.

5. The front-end loader of claim 3, wherein said intracardiac occluder comprises an occluder for treating a ventricular septal defect.

6. The front-end loader of claim 3, wherein said intracardiac occluder comprises an occluder for treating patent ductus arteriosus.

7. The front-end loader of claim 3, wherein said intracardiac occluder comprises an occluder for treating patent foramen ovale.

\* \* \* \* \*